United States Patent [19]

Müller et al.

[11] 4,310,711

[45] Jan. 12, 1982

[54] PROCESS FOR PREPARING 5-CHLORO-2-NITROPHENOL

[75] Inventors: Helmut Müller, Eschborn; Konrad Baessler, Frankfurt am Main, both of Fed. Rep. of Germany

[73] Assignee: Hoechst Aktiengesellschaft, Frankfurt am Main, Fed. Rep. of Germany

[21] Appl. No.: 183,393

[22] Filed: Sep. 2, 1980

[30] Foreign Application Priority Data

Sep. 4, 1979 [DE] Fed. Rep. of Germany ....... 2935629

[51] Int. Cl.$^3$ .............................................. C07C 79/32
[52] U.S. Cl. ................................................... 568/709
[58] Field of Search ......................................... 568/709

[56] References Cited

U.S. PATENT DOCUMENTS 3,813,446 5/1974 Jacobs ................................. 568/709
3,928,470 12/1975 Soula et al. ......................... 568/709

FOREIGN PATENT DOCUMENTS 2614264 6/1977 Fed. Rep. of Germany ...... 568/709
1581400 10/1969 France ................................. 568/709

OTHER PUBLICATIONS

"Chemiker-Zeitung", vol. 95, Jahrgang (1971), No. 7, p. 903.

*Primary Examiner*—Werren B. Lone
*Attorney, Agent, or Firm*—Curtis, Morris & Safford

[57] ABSTRACT

A process for preparing 5-chloro-2-nitrophenol from 2,4-dichloronitrobenzene and excess alkali metal hydroxide in the presence of aprotic polar solvents at 20° to 150° C.

5 Claims, No Drawings

PROCESS FOR PREPARING 5-CHLORO-2-NITROPHENOL

The present invention relates to a process for preparing 5-chloro-2-nitrophenol by reacting 2,4-dichloronitrobenzene with alkali metal hydroxides. The process product and the compound 5-chloro-2-aminophenol prepared therefrom by reduction are both intermediates for the manufacture of dyestuffs.

It is know to prepare halonitrophenols by reacting halo-2-nitrobenzenes with an alkali metal hydroxide in the presence of organic solvents (German Offenlegungsschrift No. 2,614,264). This reference states that the permittivity of the solvent used must not be higher than 25 at a temperature of from 20° to 25° C., in order to ensure a selective substitution in the ortho-position. The preferred solvents are low molecular tertiary alcohols, i.e. protic solvents, optionally containing in addition aprotic solvents with low permittivity.

It is further stated that working with anhydrous solvents is of decisive importance, for there would result a mixture of isomers when working with a solvent mixture containing relatively small quantities of water.

A disadvantage of this known process is to be seen in the fact that all components have to be introduced into the reaction vessel at the same time and that the reaction has to be run at relatively high temperature and pressure. When working with large batches, overheating may result in this method of operating, which is dangerous with ortho-nitrophenolates that are rather unstable in anhydrous state.

It has now been found that 5-chloro-2-nitrophenol can be successfully prepared from 2,4-dichloronitrobenzene and alkali metal hydroxides in the presence of an organic solvent when performing the reaction in the presence of aprotic polar solvents at 20° to 150° C., with the use of from 100 to 150% of the theory of an alkali metal hydroxide (2 to 3 mols per mol of 2,4-dichloronitrobenzene).

In view of the disclosure in the prior art it is surprising that the chlorine in ortho position is exchanged with a high degree of selectivity when using the polar aprotic solvents according to the process of the present invention and that a product free from isomers is obtained in high yields.

Preferred embodiments of the process according to the present invention will be described in greater detail hereinunder:

Suitable aprotic polar solvents are those that are sufficiently stable to the alkali metal hydroxide under the reaction conditions, for example dimethyl sulfoxide, n-methyl pyrrolidone, tetramethylene sulfone ("sulfolane"), dimethyl formamide, dimethyl acetamide or hexamethyl phosphoric acid tris-amide.

The alkali metal hydroxide (preferably sodium hydroxide or potassium hydroxide) is suitably added in solid form or as concentrated aqueous solution (about 50% strength). The alkali metal hydroxide is preferably used in an amount of from 105 to 120% of the theoretical one (2.1 to 2.4 mols, per mol of 2,4-dichloronitrobenzene). (The stoichiometric ratio is 2 mols per mol of dischloronitrobenzene, one mol being required for exchanging OH for Cl and the second mol being required for converting the phenol obtained into the phenolate).

In a particularly preferred embodiment of the present invention the alkali metal hydroxide is added at elevated temperature in solid form or as a 50% solution to a mixture of 2,4-dichloronitrobenzene, solvent and an emulsifier. The preferred reaction temperature is in the range of from 30° to 120° C.

The reaction is preferably performed under normal pressure, which facilitates the alkali metal hydroxide addition.

Upon completion of the reaction the reaction mixture is neutralized by means of a mineral acid, for example 30% hydrochloric acid. The alkali metal salt obtained is separated, suitably by filtration. The filtrate consists of an oil phase and of a solvent-water phase. The oil phase is separated, washed neutral with water and distilled under reduced pressure. The solvent-water mixture is worked up in known manner.

The following examples illustrate the invention. Percentages are by weight, unless stated otherwise.

EXAMPLE 1

768 g of 2,4-dichloronitrobenze, 880 g of dimethyl sulfoxide (=DMSO) and 2 g of a commercial emulsifier (consisting substantially of the sodium salt of an alkylbenzenesulfonate, n-butanol and small quantities of a high-boiling hydrocarbon, a sodium-alkylsulfonyl glycinate and olein) are introduced into the reaction vessel. Within 5 hours 986 g of 50% aqueous potassium hydroxide solution are added at 60° C. while stirring, and stirring is continued for 20 hours at 60° C. The pH of the reaction mixture is then adjusted to 5.5 to 6 by adding 598 g of 30% hydrochloric acid. The potassium chloride obtained is separated by filtration and washed twice with 100 g each of DMSO. The filtrate consists of a lower dark brown oily phase and an upper DMSO-water phase. The oily phase is separated and washed several times with water. The DMSO may be separated from the combined aqueous phases by distillation in vacuo and recycled to the next batch.

The oily phase consisting of crude 5-chloro-2-nitrophenol, is continuously fed at a pressure of 0.013 bar into a distillation flask heated to 120° to 125° C. The yellow colored product distilling at 115° C. is collected. 562 g (81% of the theory) of 5-chloro-2-nitrophenol, m.p. 35.5° C. are obtained, having a purity of 99.5% according to gas chromatography. The distillation residue contains dichlorodinitrodiphenyl ether and tar.

EXAMPLE 2

384 g of 2,4-dichloronitrobenzene, 600 g of tetramethylene sulfone (sulfolane) and 1 g of the emulsifier as specified in Example 1 are introduced into the reaction vessel. Within 4 hours 448 g of 50% potassium hydroxide solution are added at 110° C. After stirring for a further 21 hours at 110° C., the reaction product is adjusted to pH 5.5 to 6 with 240 g of 30% hydrochloric acid and worked up as described in Example 1. 263 g of 5-chloro-2-nitrophenol (76% of the theory) are obtained.

EXAMPLE 3

192 g of 2,4-dichloronitrobenzene, 220 g of DMSO and 0.5 ml of the emulsifier specified in Example 1 are introduced into the reaction vessel. 160 g of 50% NaOH are added at 60° C. within 1 hour and the reaction mixture is stirred for 22 hours at 60° C. Subsequently 150 ml of water are added, the mixture is stirred until the temperature has cooled to 20° C. and the red sodium salt of 5-chloro-2-nitrophenol is suction-filtered and washed three times with 50 ml portions of water. The moist salt is added to 122 g of 30% HCl yielding 5-chloro-2-nitrophenol as an oil which is separated and dried in vacuo. The yield is 151.5 g of 5-chloro-2-nitrophenol (87% of the theory), m.p. 36.5° C. having a degree of purity of 100% according to gas chromatography.

EXAMPLE 4

192 g of 2,4-dichloronitrobenzene and 250 g of DMSO are introduced into the reaction vessel. 88 g of 100% caustic soda are added at 60° C. within 1 hour and the reaction mixture is stirred for 25 hours at 60° C. The reaction product is adjusted to pH 5.5 to 6 with 140 g of 30% HCl and worked up as described in Example 1. The yield is 136 g of 5-chloro-2-nitrophenol (78% of the theory).

What is claimed is:

1. A process for the preparation of 5-chloro-2-nitrophenol which comprises reacting 2,4-dichloronitrobenzene with 2 to 3 mols of alkali metal hydroxide per mol of 2,4-dichloronitrobenzene in the presence of an organic solvent said reaction being conducted in the presence of an aprotic polar solvent selected from the group consisting of dimethyl sulfoxide, N-methyl pyrrolidone, tetramethylene sulfone, dimethyl formamide, dimethyl acetamide and hexamethyl phosphoric acid trisamide at a temperature in the range of 30° C. to 120° C. and at normal pressure.

2. The process of claim 1 wherein 2.1 to 2.4 mols of alkali metal hydroxide are reacted per mol of 2,4-dichloronitrobenzene.

3. The process of claim 1 or 2 wherein the alkali metal hydroxide is added in the form of a 50% aqueous solution.

4. The process of claim 1 wherein the alkali metal hydroxide is sodium hydroxide or potassium hydroxide.

5. The process of claim 1 wherein an emulsifier is added to the reaction mixture.